US00RE43748E

(19) United States
(12) Reissued Patent
Furuta et al.

(10) Patent Number: US RE43,748 E
(45) Date of Reissued Patent: Oct. 16, 2012

(54) NITROGEN-CONTAINING HETEROCYCLIC CARBOXAMIDE DERIVATIVES OR SALTS THEREOF AND ANTIVIRAL AGENTS COMPRISING THE SAME

(75) Inventors: Yousuke Furuta, Tokyo (JP); Hiroyuki Egawa, Tokyo (JP); Nobuhiko Nomura, Tokyo (JP)

(73) Assignee: Toyama Chemical Co., Ltd., Tokyo (JP)

(21) Appl. No.: 12/869,074

(22) Filed: Aug. 26, 2010

Related U.S. Patent Documents

Reissue of:
(64) Patent No.: 6,787,544
Issued: Sep. 7, 2004
Appl. No.: 09/788,992
Filed: Feb. 20, 2001

U.S. Applications:
(63) Continuation-in-part of application No. PCT/JP99/04429, filed on Aug. 18, 1999.

(30) Foreign Application Priority Data

Aug. 20, 1998 (JP) ..... 10-250441
May 26, 1999 (JP) ..... 11-145922

(51) Int. Cl.

| | |
|---|---|
| ***C07D 241/28*** | (2006.01) |
| ***A61K 31/495*** | (2006.01) |
| ***A61K 31/50*** | (2006.01) |
| ***A61K 31/505*** | (2006.01) |
| ***A61K 31/53*** | (2006.01) |
| *C07D 237/04* | (2006.01) |
| *C07D 237/06* | (2006.01) |
| *C07D 239/20* | (2006.01) |
| *C07D 239/24* | (2006.01) |
| *C07D 253/06* | (2006.01) |
| *C07D 253/065* | (2006.01) |

(52) U.S. Cl. ..... 544/408; 544/180; 544/182; 544/219; 544/220; 544/239; 544/315; 544/318; 544/319; 514/241; 514/242; 514/247; 514/252.1; 514/255.06; 514/269

(58) Field of Classification Search ..... 544/180, 544/182, 219, 220, 239, 319, 408; 514/241, 514/242, 247, 252.1, 255.06, 269
See application file for complete search history.

(56) References Cited

U.S. PATENT DOCUMENTS

| | | | |
|---|---|---|---|
| 3,631,036 | A | 12/1971 | Kim et al. |
| 3,745,161 | A | 7/1973 | Shen et al. |
| 4,404,203 | A | 9/1983 | Sircar et al. |
| 4,545,810 | A | 10/1985 | Pyne et al. |
| 4,565,814 | A | 1/1986 | Kan et al. |
| 4,661,145 | A | 4/1987 | Fujimoto et al. |
| 5,420,130 | A | 5/1995 | George et al. |
| 5,459,142 | A | 10/1995 | Tone et al. |
| 5,597,823 | A | 1/1997 | Meyer et al. |
| 6,159,980 | A | 12/2000 | Arvanitis et al. |

FOREIGN PATENT DOCUMENTS

| | | | |
|---|---|---|---|
| EP | 0 023 358 | A1 | 7/1980 |
| GB | 1198688 | A | 7/1970 |
| HU | P9401512 | | 5/1994 |
| JP | 56-020576 | A | 2/1981 |
| JP | 09216883 | A2 | 8/1997 |

OTHER PUBLICATIONS

Lee et al. Journal of Medicinal Chemistry 26(2), 283-286, 1983.
Bambury et al. Journal of Medicinal Chemistry 27(12), 1613-1621, 1984.
Sircar et al. Journal of Medicinal Chemistry 28 (10), 1405-1413, 1985.
Wermuth et al. Journal of Medicinal Chemistry 32(3), 528-537, 1989.
Kuraishi et al. Chemical & Pharmaceutical Bulletin 6, 551-556, 1958.
Haider et al. Pharmazie 44(9), 598-601, 1989.
Reid et al. Archiv der Pharmazie 321(9), 527-32, 1988.
Knotz et al. Mikrochimica Acta 1, 81-84, 1874.
Mahy, Antiviral Research 36, 75-80, 1997.
J. Daunis and M. Follet, Bulletin de la Societe Chimique de France, No. 3-4, Pt. 2, pp. 864-870 (1975).
M. Krystal et al., Antiviral Chemistry & Chemotherapy, vol. 7, No. 6, pp. 353-360 (Nov. 1996).
Dornow et al. Ber 97 (12), 3349-3353, 1964.
Hungarian Search Report issued on Nov. 28, 2002 in Hungarian Patent Application No. P0103453.

*Primary Examiner* — Venkataraman Balasubramanian
(74) *Attorney, Agent, or Firm* — Oblon, Spivak, McClelland, Maier & Neustadt, L.L.P.

(57) ABSTRACT

Nitrogen-containing heterocyclic carboxamide derivatives represented by the following general formula:

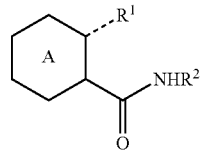

wherein ring A is a substituted or unsubstituted pyrazine, pyrimidine, pyridazine or triazine ring; $R^1$ is O or OH; $R^2$ is a hydrogen atom, an acyl group or a substituted or unsubstituted carbamoylalkyl or carboxyalkyl group; and the broken line represents a single bond or a double bond; or salts thereof are useful for preventing and treating virus infections and especially influenza virus infections.

24 Claims, No Drawings

NITROGEN-CONTAINING HETEROCYCLIC CARBOXAMIDE DERIVATIVES OR SALTS THEREOF AND ANTIVIRAL AGENTS COMPRISING THE SAME

Matter enclosed in heavy brackets [ ] appears in the original patent but forms no part of this reissue specification; matter printed in italics indicates the additions made by reissue.

CROSS-REFERENCE TO RELATED APPLICATIONS

This application *is Reissue of non-provisional application Ser. No. 09/788,992, filed on Feb. 20, 2001, now U.S. Pat. No. 6,787,544, which* is a continuation-in-part of PCT/JP99/04429, filed on Aug. 18, 1999, of which the entire disclosure including specification, claims, drawings and summary are incorporated herein by reference in its entirety.

TECHNICAL FIELD

The present invention relates to antiviral agents comprising a nitrogen-containing heterocyclic carboxamide derivative or a salt thereof.

BACKGROUND ART

Nowadays, antiviral agents are selected and put to use in accordance with the objective viruses. For instance, Acyclovir and Vidarabine are used against herpes viruses; Ganciclovir and Foscarnet are used against cytomegalo virus; and interferon is used against hepatitis viruses.

Influenza virus is a central virus of the cold syndrome, which has attacked human being periodically to cause many deaths amounting to tens millions. Although the number of deaths shows a tendency of decrease in the recent years owing to the improvement in hygienic and nutritive conditions, the prevalence of influenza is repeated every year, and it is apprehended that a new virus may appear to cause a wider prevalence.

For prevention of influenza virus, vaccine is used widely, in addition to which low molecular weight substances such as Amantadine and Ribavirin are also used.

Amantadine is used for prevention and treatment of influenza. Its function mechanism is said to consist in inhibiting the fusion between influenza virus and cell membrane, and it is effective against A-type influenza virus. Its problems are, however, that it is ineffective against B type influenza virus, its resistant virus appears, and it causes side effects such as nerve disturbance. Although Rimantadine which is a derivative of Amantadine has a more improved antiviral activity, the problem of side effect is not overcome by it. Ribavirin which is a guanosine derivative shows a viral RNA polymerase-inhibitory activity and is effective upon A type and B type influenza viruses. Its internal use, however, brings about no sufficient clinical effect.

The present invention provides an antiviral agent exhibiting a preventive effect and a therapeutic effect against various viruses, especially influenza viruses.

DISCLOSURE OF THE INVENTION

The present inventors have conducted researches and studies on compounds showing an antiviral activity against various viruses, especially influenza viruses. As a result, it has been found that pyrazine carboxamide derivatives have an anti-influenza virus activity. The inventors conducted further studies to find that nitrogen-containing heterocyclic carboxamide derivatives represented by the following general formula [1]:

[1]

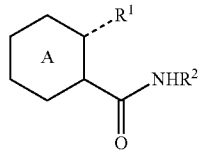

wherein ring A represents a substituted or unsubstituted pyrazine, pyrimidine, pyridazine or triazine ring; $R^1$ represents O or OH; $R^2$ represents a hydrogen atom, an acyl group or a substituted or unsubstituted carbamoylalkyl or carboxyalkyl group; and the broken line represents a single bond or a double bond; or salts thereof exhibit an excellent antiviral activity against A-, B- and C-type of influenza viruses and other various viruses, these compounds have low cytotoxicity and are useful as an antiviral agents of high safety, as well as that novel N-containing heterocyclic carboxamide derivatives represented by the following general formula [1a]:

[1a]

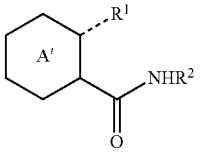

wherein ring A' represents a pyrazine ring substituted with a halogen atom, a hydroxyl group or an oxide group; $R^1$ represents O or OH; $R^2$ represents a hydrogen atom, an acyl group or a substituted or unsubstituted carbamoylalkyl or carboxyalkyl group; and the broken line represents a single bond or a double bond; or salts thereof exhibit an excellent antiviral activity. Based on these findings, the present invention has been accomplished.

The present invention will be described in detail below.

Unless otherwise indicated, the term "halogen atom" used in this specification means a fluorine atom, a chlorine atom, a bromine atom or an iodine atom; the term "alkyl group" means a straight or branched chain $C_{1-6}$ alkyl group such as methyl, ethyl, n-propyl, isopropyl, n-butyl, isobutyl, sec-butyl, tert-butyl, pentyl and the like; the term "alkenyl group" means a straight or branched chain $C_{2-6}$ alkenyl group such as vinyl, allyl and the like; the term "cycloalkyl group" means a $C_{3-6}$ cycloalkyl group such as cyclopropyl, cyclopentyl, cyclohexyl and the like; the term "alkoxy group" means a straight or branched chain $C_{1-6}$ alkyl-O— group such as methoxy, ethoxy, n-propoxy, isopropoxy, n-butoxy, isobutoxy, sec-butoxy, tert-butoxy, pentyloxy and the like; the term "cycloalkyloxy group" means a $C_{3-6}$ cycloalkyl-O— group such as cyclopropyloxy, cyclopentyloxy, cyclohexyloxy and the like; the term "alkylthio group" means a straight or branched chain $C_{1-6}$ alkyl-S— group such as methylthio, ethylthio, n-propylthio, isopropylthio, n-butylthio, isobutylthio, sec-butylthio, tert-butylthio, pentylthio and the like; the term "alkylamino group" means an amino group substituted with one or more straight or branched chain $C_{1-6}$ alkyl groups such as methylamino, ethylamino, propylamino, butylamino, pentylamino, hexylamino, dimethylamino, diethylamino, methylethylamino, dipropylamino, dibutylamino, dipentylamino and the like; the term "cycloalkylamino group" means a $C_{3-6}$ cycloalkyl-NH— group such as cyclopropylamino, cyclopentylamino, cyclohexylamino and the like; the term "halogenoalkyl group" means a halogen-substituted $C_{1-6}$ alkyl group such as trifluoromethyl, trichloromethyl, chloromethyl and the like; the term "aryl group" means a phenyl group, a naphthyl group and the like; the term "aryloxy group" means an aryl-O— group such as phenyloxy, naphthyloxy and the like; the term "arylthio group" means an aryl-S— group such as phenylthio, naphthylthio and the like; the term "arylamino group" means an aryl-NH— group such as phenylamino, naphthylamino and the like; the term "acyl group" means a $C_{2-5}$ alkanoyl group such as formyl, acetyl, propionyl, butyryl, isobutyryl, valeryl and the like and an aroyl group such as benzoyl, naphthoyl and the like; the term "alkoxycarbonyl group" means a straight or branched chain $C_{1-6}$ alkoxycarbonyl group such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl and the like; the term "alkylcarbamoyl group" means a carbamoyl group substituted with one or more straight or branched chain $C_{1-6}$ alkyl groups such as methylcarbamoyl, dimethylcarbamoyl and the like; the term "carbamoylalkyl group" means a straight or branched chain $C_{1-6}$ alkyl group substituted with a carbamoyl group such as carbamoylmethyl, carbamoylethyl, carbamoylisopropyl and the like; the term "carboxyalkyl group" means a straight or branched chain $C_{1-6}$ alkyl group substituted with a carboxyl group such as carboxymethyl, carboxylethyl, carboxyisopropyl and the like; the term "heterocyclic group" means a 4-, 5- or 6-membered ring or a fused ring thereof having, as the hetero atoms constituting said ring, at least one heteroatoms selected from the group consisting of oxygen atom, nitrogen atom and sulfur atom, such as oxetanyl, thietanyl, azetidinyl, furyl, pyrrolyl, thienyl, oxazolyl, isoxazolyl, imidazolyl, thiazolyl, isothiazolyl, pyrrolidinyl, benzofuranyl, benzothiazolyl, pyridyl, quinolyl, pyrimidinyl and morpholinyl; and the term "oxide group" means an oxygen atom linked to a nitrogen atom in a ring. The term "lower" means that the number of carbon atoms is 1 to 6.

The protecting group for carboxyl group includes any groups which can conventionally be used as a protecting group for carboxyl group. The examples thereof include alkyl groups such as methyl, ethyl, n-propyl, isopropyl, 1,1-dimethylpropyl, n-butyl, tert-butyl and the like; aryl groups such as phenyl, naphthyl and the like; aralkyl groups such as benzyl, diphenylmethyl, trityl, p-nitrobenzyl, p-methoxybenzyl, bis(p-methoxyphenyl)methyl and the like; acylalkyl groups such as acetylmethyl, benzoylmethyl, p-nitro-benzoylmethyl, p-bromobenzoylmethyl, p-methanesulfonylbenzoylmethyl and the like; oxygen-containing heterocyclic groups such as 2-tetrahydropyranyl, 2-tetrahydrofuranyl and the like; halogeno-alkyl groups such as 2,2,2-trichloroethyl and the like; alkylsilylalkyl groups such as 2-(trimethylsilyl)ethyl and the like; acyloxyalkyl groups such as acetoxymethyl, propionyloxymethyl, pivaloyloxymethyl and the like; nitrogen-containing heterocyclic alkyl groups such as phthalimidomethyl, succinimidomethyl and the like; cycloalkyl groups such as cyclohexyl and the like; alkoxyalkyl groups such as methoxymethyl, ethoxymethyl, 2-(trimethylsilyl)ethoxymethyl and the like; aralkoxyalkyl groups such as benzyloxymethyl and the like; alkylthioalkyl groups such as methylthiomethyl, 2-methylthioethyl and the like; arylthioalkyl groups such as phenylthiomethyl and the like; alkenyl groups such as 1,1-dimethyl-2-propenyl, 3-methyl-3-butenyl, allyl and the like; substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like; etc.

In general formula [1], ring A represents a pyrazine ring, a pyrimidine ring, a pyridazine ring or a triazine ring. More specifically, ring A represents any of the following structures:

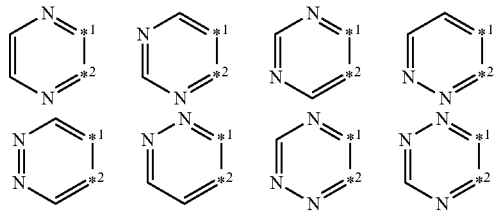

In the structures above, the mark *1 expresses the position of substitution with $R^1$, and the mark *2 expresses the position of substitution with —C(=O)NHR$^2$.

The carbamoylalkyl or carboxyalkyl group represented by $R^2$ may be substituted with at least one substituent selected from the group consisting of halogen atoms; alkyl groups unsubstituted or substituted with hydroxyl, alkoxy, alkylthio, aryl, amino or alkylamino groups; halogenoalkyl groups; alkenyl groups; cycloalkyl groups; hydroxyl groups; alkoxy groups; cycloalkyloxy groups; alkoxycarbonyl groups; mercapto groups; alkylthio groups unsubstituted or substituted with one or more aryl groups; aryl groups; aryloxy groups; arylthio groups; arylamino groups; cyano groups; nitro groups; amino groups unsubstituted or substituted with one or more acyl groups; alkylamino groups; cycloalkylamino groups; acyl groups; hydrazino groups; carboxyl groups; carbamoyl groups; thiocarbamoyl groups; alkylcarbamoyl groups and heterocyclic groups.

Of ring A represented by general formula [1], preferred are pyrazine ring, pyrimidine ring and triazine ring, and more preferred is pyrazine ring. The substituent on ring A includes groups selected from the group consisting of halogen atoms; alkyl groups unsubstituted or substituted with one or more hydroxyl, alkoxy, alkylthio, aryl, amino or alkylamino groups; halogenoalkyl groups; alkenyl groups; cycloalkyl groups; hydroxyl groups; alkoxy groups; cycloalkyloxy groups; alkoxycarbonyl groups; mercapto groups; alkylthio groups unsubstituted or substituted with one or more aryl groups; aryl groups; aryloxy groups; arylthio groups; arylamino groups; cyano groups; nitro groups; amino groups unsubstituted or substituted with one or more acyl groups; alkylamino groups; cycloalkylamino groups; acyl groups; hydrazino groups; carboxyl groups; carbamoyl groups; thiocarbamoyl groups, alkylcarbamoyl groups and heterocyclic groups. Ring A can have one or more of the above-mentioned substituents. Further, the substituent on ring A is preferably linked to carbon atom of the ring.

The salt of the compound of general formula [1] includes any usually known salts formed at the site of basic groups such as amino group and salts formed at the site of acidic group such as hydroxyl and carboxyl groups. The salts formed at the site of basic group include salts of mineral acids such as hydrochloric acid, hydrobromic acid, sulfuric acid and the like; salts of organic carboxylic acids such as tartaric acid, formic acid, citric acid, trichloroacetic acid, trifluoroacetic acid and the like, and salts of sulfonic acids such as methanesulfonic acid, benzenesulfonic acid, p-toluenesulfonic acid, mesitylenesulfonic acid, naphthalenesulfonic acid and the like. The salts formed at the site of acidic group include salts of alkali metals such as sodium, potassium and the like; salts of alkaline earth metals such as calcium, magnesium and the like; ammonium salts; and salts of nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, N,N'-dibenzylethylenediamine and the like. Among the salts mentioned above, preferred are pharmacologically acceptable ones.

Typical compounds represented by general formula [1] are shown in Tables 1 to 4.

In the tables shown below, the abbreviations have the following meanings:

Me: methyl

Et: ethyl iPr: isopropyl tBu: tert-butyl,

Ph: phenyl

Ac: acetyl

Bz: benzoyl

R2a: —CH (COOH) $CH_2COOH$

R2b: —CH ($CH_3$) CONHCH ($CH_3$) COOH

TABLE 1

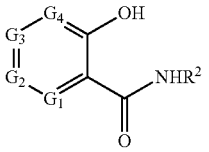

| No. | $G_1$ | $G_2$ | $G_3$ | $G_4$ | $R^2$ |
|---|---|---|---|---|---|
| 1 | N | CH | CH | N | H |
| 2 | N | CH | CH | N→O | H |
| 3 | N | CH | CH | N | Ac |
| 4 | N | CH | CH | N | Bz |
| 5 | N | CH | CH | N | C(O)tBu |
| 6 | N | CH | CH | N | $CH_2CONH_2$ |
| 7 | N | CH | C—Cl | N | H |
| 8 | N | CH | C—Br | N | H |
| 9 | N | CH | C—OH | N | H |
| 10 | N | CH | C—OMe | N | H |
| 11 | N | CH | C—OEt | N | H |
| 12 | N | CH | C—OiPr | N | H |
| 13 | N | CH | C—O-cyclopropyl | N | H |
| 14 | N | CH | C—NHMe | N | H |
| 15 | N | CH | C—$NMe_2$ | N | H |
| 16 | N | CH | C—NH-cyclopropyl | N | H |
| 17 | N | CH | C—NHAc | N | H |
| 18 | N | CH | C—NHBz | N | H |
| 19 | N | CH | C—NHPh | N | H |
| 20 | N | CH | C—SH | N | H |
| 21 | N | CH | C—SMe | N | H |
| 22 | N | CH | C—COOH | N | H |
| 23 | N | CH | C—COOMe | N | H |
| 24 | N | CH | C—COOEt | N | H |
| 25 | N | CH | C—$CONH_2$ | N | H |
| 26 | N | CH | C—$CSNH_2$ | N | H |
| 27 | N | CH | C—CONHMe | N | H |
| 28 | N | CH | C—$CONMe_2$ | N | H |
| 29 | N | CH | C—Et | N | H |
| 30 | N | CH | C—iPr | N | H |
| 31 | N | CH | C—$CCl_3$ | N | H |
| 32 | N | CH | C—$CF_3$ | N | H |
| 33 | N | CH | C—$CH_2Cl$ | N | H |
| 34 | N | CH | C—$CH_2$—SMe | N | H |
| 35 | N | CH | C—$CH_2$—OMe | N | H |
| 36 | N | CH | C—$CH_2$—Ph | N | H |
| 37 | N | CH | C—$CH_2$—$NH_2$ | N | H |
| 38 | N | CH | C—$CH_2$—OH | N | H |
| 39 | N | CH | C—$CH_2$—NHMe | N | H |
| 40 | N | CH | C—CH═$CH_2$ | N | H |

TABLE 2

| No. | $G_1$ | $G_2$ | $G_3$ | $G_4$ | $R^2$ |
|---|---|---|---|---|---|
| 41 | N | CH | C—Ph | N | H |
| 42 | N | CH | C-pyridin-3-yl | N | H |
| 43 | N | CH | C-furan-2-yl | N | H |
| 44 | N | CH | C-thiophen-2-yl | N | H |
| 45 | N | CH | C-thiazol-2-yl | N | H |
| 46 | N | CH | C-pyrrolidin-1-yl | N | H |
| 47 | N | CH | C-piperidin-1-yl | N | H |
| 48 | N | CH | C-morpholin-4-yl | N | H |
| 49 | N | CH | C—CN | N | H |
| 50 | N | CH | C—$NO_2$ | N | H |
| 51 | N | CH | C—Bz | N | H |
| 52 | N | CH | C—Ac | N | H |
| 53 | N | C—$CONH_2$ | C—$NH_2$ | N | H |
| 54 | N | C—$NH_2$ | C—COOH | N | H |
| 55 | N | C—$NH_2$ | C—COOMe | N | H |
| 56 | N | C—Cl | C—COOMe | N | H |
| 57 | N | C—OMe | C—Me | N | H |
| 58 | N | C—COOH | C—Me | N | H |
| 59 | N | C—COOH | C—NHMe | N | H |
| 60 | N | C—COOMe | C—Cl | N | H |
| 61 | N | C—COOMe | C-piperidin-1-yl | N | H |
| 62 | N | C—OMe | C—CN | N | H |
| 63 | N | C—Me | C—Me | N | H |
| 64 | N | C—Ph | C—Ph | N | H |
| 65 | N | C—F | CH | N | H |
| 66 | N | C—Cl | CH | N | H |
| 67 | N | C—Br | CH | N | H |
| 68 | N | C—OH | CH | N | H |
| 69 | N | C—OMe | CH | N | H |
| 70 | N | C—OET | CH | N | H |
| 71 | N | C—O-iPr | CH | N | H |
| 72 | N | C-cyclopropyl | CH | N | H |
| 73 | N | C—OPh | CH | N | H |
| 74 | N | C—$NH_2$ | CH | N | H |
| 75 | N | C—NHMe | CH | N | H |
| 76 | N | C—$NMe_2$ | CH | N | H |
| 77 | N | C-cyclopropyl | CH | N | H |
| 78 | N | C—NHPh | CH | N | H |
| 79 | N | C—NHAc | CH | N | H |
| 80 | N | C—NHBz | CH | N | H |

TABLE 3

| No. | $G_1$ | $G_2$ | $G_3$ | $G_4$ | $R^2$ |
|---|---|---|---|---|---|
| 81 | N | C—COOMe | CH | N | H |
| 82 | N | C—$CF_2$ | CH | N | H |
| 83 | N | C—Ph | CH | N | H |
| 84 | N | C-pyridin-4-yl | CH | N | H |
| 85 | N | C—CN | CH | N | H |
| 86 | N | C—$NO_2$ | CH | N | H |
| 87 | CH | N | CH | N | H |
| 88 | CH | N | CH—Me | N | H |
| 89 | CH | N | C—Et | N | H |
| 90 | CH | N | C-iPr | N | H |
| 91 | CH | N | C—F | N | H |
| 92 | CH | N | C—Cl | N | H |
| 93 | CH | N | C—Br | N | H |
| 94 | CH | N | C—Ph | N | H |
| 95 | CH | N | C—OH | N | H |
| 96 | CH | N | C—OMe | N | H |
| 97 | CH | N | C—OEt | N | H |
| 98 | CH | N | C—OiPr | N | H |
| 99 | CH | N | C—SH | N | H |
| 100 | CH | N | C—SMe | N | H |
| 101 | CH | N | C—S—$CH_2Ph$ | N | H |
| 102 | CH | N | C—SPh | N | H |
| 103 | CH | N | C—$NH_2$ | N | H |
| 104 | CH | N | C—NHMe | N | H |
| 105 | CH | N | C—$NMe_2$ | N | H |
| 106 | CH | N | C-piperidin-1-yl | N | H |
| 107 | CH | N | C—NH—Ph | N | H |

TABLE 3-continued

| No. | $G_1$ | $G_2$ | $G_3$ | $G_4$ | $R^2$ |
|---|---|---|---|---|---|
| 108 | C—OH | N | C—SH | N | H |
| 109 | C—OH | N | C—$NH_2$ | N | H |
| 110 | C—Me | N | C—OH | N | H |
| 111 | N | CH | N | CH | H |
| 112 | N | C—F | N | CH | H |
| 113 | N | C—Cl | N | CH | H |
| 114 | N | C—F | N | C—Me | H |
| 115 | N | C—Cl | N | C—Et | H |
| 116 | N | C—OMe | N | C—OH | H |
| 117 | N | C—$NH_2$ | N | C—OH | H |
| 118 | N | C—NHAc | N | C—OH | H |
| 119 | N | C—SH | N | C—OH | H |
| 120 | N | C—SMe | N | C—OH | H |

TABLE 4

| No. | $G_1$ | $G_2$ | $G_3$ | $G_4$ | $R^2$ |
|---|---|---|---|---|---|
| 121 | N | C—Me | N | C—NHMe | H |
| 122 | N | C—Ph | N | C—OH | H |
| 123 | N | C—Me | N | C—OH | H |
| 124 | N | C—Me | N | C—S—Ph | H |
| 125 | N | C—Me | N | C—Cl | H |
| 126 | N | C—Me | N | C—OMe | H |
| 127 | N | C—Me | N | C—OPh | H |
| 128 | N | C—Me | N | C-morpholin-4-yl | H |
| 129 | CH | CH | N | N | H |
| 130 | CH | C—OH | N | N | H |
| 131 | CH | C—Me | N | N | H |
| 132 | N | CH | N | N | H |
| 133 | N | C—Cl | N | N | H |
| 134 | N | C—Me | N | N | H |
| 135 | N | C—OMe | N | N | H |
| 136 | N | C—$NH_2$ | N | N | H |
| 137 | N | C—NHAc | N | N | H |
| 138 | N | C-pyridin-4-yl | N | N | H |
| 139 | N | N | CH | N | H |
| 140 | N | N | C—Br | N | H |
| 141 | N | N | C—OH | N | H |
| 142 | N | N | C—OiPr | N | H |
| 143 | N | N | C—NHPh | N | H |
| 144 | N | N | C-thiazol-2-yl | N | H |
| 145 | N | N | C—SH | N | H |
| 146 | N | N | C—SMe | N | H |
| 147 | N | N | C—Cl | N | H |
| 148 | N | N | C—$NHNH_2$ | N | H |
| 149 | N | N | C—Ph | N | H |
| 150 | N | N | C-pyridin-2-yl | N | H |
| 151 | N | N | C-thiophen-2-yl | N | H |
| 152 | N | N | C—NHMe | N | H |
| 153 | N | N | C—$NMe_2$ | N | H |
| 154 | N | CH | C—F | N | H |
| 155 | N | CH | CH | N | R2a |
| 156 | N | CH | CH | N | R2a |

The nitrogen-containing heterocyclic carboxamide derivatives represented by general formula [1] or salts thereof are commercially available or can be produced according to any of known processes or analogous processes or by a combination thereof. As the papers describing the production processes thereof, J. Am. Chem. Soc., 71, 78 (1949); J. Am. Chem. Soc., 78, 242-244 (1956); J. Heterocycl. Chem., 15(4), 665-670 (1978); J. Chem. Soc., 1379 (1955); U.S. Pat. No. 5,597,823; etc. can be referred to.

More specifically, the nitrogen-containing heterocyclic carboxamide derivatives represented by general formula [1] or salts thereof can be produced according to the following Production Processes 1 to 3.

Production Process 1

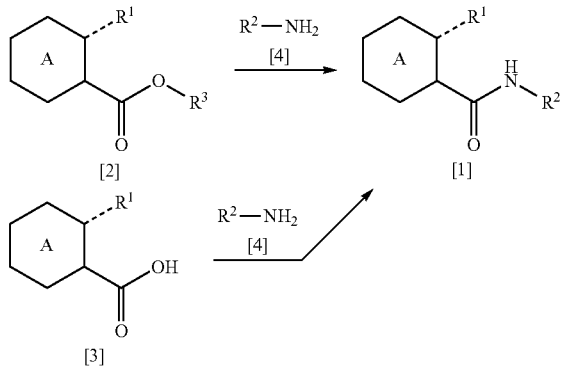

wherein $R^1$, $R^2$, ring A and broken line are as defined above, and $R^3$ represents a protecting group for carboxyl group.

(1-a)

A compound of general formula [1] can be obtained by reacting a compound of general formula [2] with a compound of general formula [4].

The solvent which can be used in this reaction is not particularly limited, so far as it causes no adverse effect on the reaction. The examples of the solvent include alcohols such as methanol, ethanol, isopropyl alcohol and the like; halogenated hydrocarbons such as dichloromethane, chloroform, dichlorocthane and the like; aromatic hydrocarbons such as benzene, toluene, xylene and the like; ethers such as dioxane, tetrahydrofuran, anisole, diethylene glycol diethyl ether, dimethyl cellosolve and the like; nitriles such as acetonitrile and the like; amides such as N,N-dimethylformamide, N,N-dimethylacetamide and the like; and sulfoxides such as dimethyl sulfoxide and the like. These solvents can be used in admixture.

The compound of general formula [4] is used at least in an equimolar amount to the compound of general formula [2], and preferably in an amount of 1.0-5.0 mole per mole of the compound of general formula [2].

This reaction can be carried out usually at 0-100° C. and preferably at 20-80° C., for a period of 5-24 hours and preferably for 30 minutes to 10 hours.

(1-b)

A compound of general formula [1] can be obtained by subjecting a compound of general formula [3] and a compound of general formula [4] to a dehydrating condensation reaction.

The solvent which can be used in this reaction is not particularly limited, so far as it causes no adverse effect on the reaction. The examples of the solvent include ethers such as dioxane, tetrahydrofuran, anisole, diethylene glycol diethyl ether, dimethyl cellosolve and the like; halogenated hydrocarbons such as dichloromethane, chloroform, dichloroethane and the like; and amides such as N,N-dimethylformamide, N,N-dimethylacetamide and the like. These solvents can be used in admixture.

The compound of general formula [4] can be used at least in an equimolar amount to the compound of general formula [3] and preferably in an amount of 1.0-2.0 mole per mole of the compound of general formula [3].

The dehydrating condensing agent which can be used in this reaction includes, for example, 1,3-dicyclohexyl carbodiimide, N,N'-carbonyl diimidazole, 1-ethyl-3-(3'-dimethylaminopropyl)carbodiimide and the like.

The dehydrating condensing agent can be used at least in an equimolar amount to the compound of general formula [3] and preferably in an amount of 1.0-2.0 mole per mole of the compound of general formula [3].

This reaction can be carried out usually at 0-100° C. and preferably at 20-60° C., for a period of 5 minutes to 24 hours and preferably for 30 minutes to 10 hours.

Production Process 2

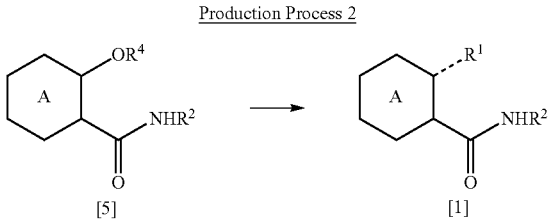

wherein $R^1$, $R^2$, ring A and broken line are as defined above, and $R^4$ represents a lower alkyl group.

A compound of general formula [1] can be obtained by subjecting a compound of general formula [5] to alkyl-ether scission.

More specifically, in a case where $R^4$ is a methyl group, the reaction can be carried out according to the description of PROTECTIVE GROUPS IN ORGANIC SYNTHESIS, Second edition, JOHN WILEY & SONS, pp. 145-199 (1991) or by an analogous method.

Production Process 3

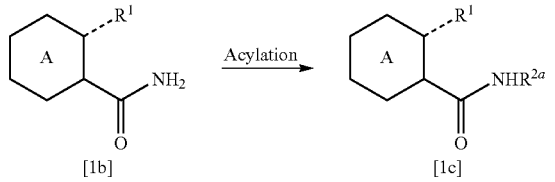

wherein $R^1$, ring A and broken line are as defined above, and $R^2$a represents an acyl group.

A compound of general formula [1c] can be obtained by subjecting a compound of general formula [1b] to acylation in the presence of an acid-eliminating agent.

The solvent which can be used in this reaction is not particularly limited, so far as it causes no adverse effect on the reaction. The examples of the solvent include ethers such as dioxane, tetrahydrofuran, anisole, diethylene glycol diethyl ether, dimethyl cellosolve and the like; aromatic hydrocarbons such as benzene, toluene, xylene and the like; halogenated hydrocarbons such as dichloromethane, chloroform, dichloroethane and the like; amides such as N,N-dimethylformamide, N,N-dimethylacetamide and the like; water; etc. These solvents can be used in admixture.

The acylating agent can be used at least in an equimolar amount to the compound of general formula [1b] and preferably in an amount of 1.0-2.0 mole per mole of the compound of general formula [1b].

The acid-eliminating agent used in this reaction includes, for example, pyridine, triethyl-amine, sodium hydrogen carbonate and the like.

The acid-eliminating agent can be used at least in an equimolar amount to the compound of general formula [1b] and preferably in an amount of 1.0-2.0 mole per mole of the compound of general formula [1b].

This reaction can be carried out usually at 0-100° C. and preferably at 20-60° C., for a period of 5 minutes to 24 hours and preferably for 30 minutes to 10 hours.

In the Production Processes 1-3, the compounds of general formula [2], [3], [4], [5] and [1b] can be replaced with their salt, respectively. As the salts, the same ones as mentioned for the compound of general formula [1] can be used.

Some of the compounds of general formulas [2], [3], [4], [5] and [1b] and salts thereof may have various isomers such as optical isomers and position isomers, and solvated products. In such cases, any of these isomers and solvates may be used in the present invention.

The compound of general formula [1c] thus obtained can be converted to salts thereof. The salts include the same ones as mentioned for the compound of general formula [1].

The objective viruses of the antiviral agent comprising the nitrogen-containing heterocyclic carboxamide derivative represented by general formula [1] or salt thereof according to the present invention include A-, B- and C-type influenza viruses, papilloma virus, adeno virus, A type hepatitis virus, B type hepatitis virus, C type hepatitis virus, bovine viral diarrhea virus (surrogate virus for C type hepatitis virus), polio virus, echovirus, Coxsackie virus, entero virus, rhino virus, rota virus, Newcastle disease virus, mumps virus, vesicular stomatitis virus, respiratory syncytial virus, and Japanese encephalitis virus. The antiviral agent of the present invention exhibits an especially high effect against influenza viruses.

By combining the nitrogen-containing heterocyclic carboxamide derivatives of the present invention represented by general formula [1] or salts thereof with conventional known excipients, adjuvants and additives, pharmaceutical preparations such as solutions, suspensions, powders, granules, fine granules, tablets, capsules, syrups, elixirs, spirits, troches, gargles, aerosols, etc. can be obtained. These pharmaceutical preparations can be administered either orally or non-orally, namely by injection, percutaneous administration, intrarectal administration, intranarial administration, etc.

The method of administration, dosage and frequency of administration of the antiviral agent of the present invention can be properly selected depending upon the age, body weight and symptom of the patient. Usually 1 to 10 mg/kg of the nitrogen-containing heterocyclic carboxamide derivative or a salt thereof can be administered to an adult either at once or in several portions.

Next, antiviral activity and cytotoxicity of the nitrogen-containing heterocyclic carboxamide derivatives of the present invention represented by general formula [1] or salts thereof will be explained.

Sample:

A nitrogen-containing heterocyclic carboxamide derivative represented by general formula [1] or a salt thereof was dissolved in dimethyl sulfoxide to prepare a solution having a concentration of 10 mg/mL. At the time of use, the solution was diluted with a culture medium to a predetermined concentration and then put to use.

As the host cell of influenza virus, MDCK cell (canine kidney cell) was used. For the cytotoxicity test, Vero cell (monkey kidney cell) was used.

Culture medium:

In the multiplication of MDCK cell and Vero cell and in the cytotoxicity test using Vero cell, E'-MEM (product of Nissui) to which 10% fetal bovine serum had been added was used.

In the measurement of antiviral activity, E'-MEM (product of Nissui) to which 1% bovine serum albumin had been added was used.

Test Example 1

(Anti-influenza Activity)

MDCK cells were seeded to a 6-well plate (product of CORNING) at $5\times10^5$ cells/well, and cultured overnight at 35° C. in 5% $CO_2$-air atmosphere. Then, the cultured MDCK cells on the plate was treated with influenza virus A/PR/8/34 strain diluted with a serum-free culture medium at the concentration of 200 PFU/mL, at 0.5 mL/well for one hour to achieve inoculation and adsorption. After completion of the inoculation and adsorption, an E'-MEM culture medium containing 0.6% Agar Noble, 1% bovine serum albumin and 3 μg/mL acetyltrypsin and also containing a test compound at a prescribed concentration was added to the cells. After sufficient coagulation, the plate was turned upside down, and cultured for 3 days. After completion of the culture, the alive cells were dyed with 1% Neutral Red. Then, cells were fixed with 10% formalin. The agar medium was removed therefrom with running water. Thereafter, the number of plaques was counted. The plaque inhibition rate was expressed in percentage calculated in comparison with control containing no test compound.

The results are shown in Table 5, wherein the test compound number are the same as those in Tables 1 to 4.

TABLE 5

| No. | Concentration of test compound added (μg/mL) | Inhibition rate (%) |
|---|---|---|
| 1 | 1 | 91.9 |
| 2 | 100 | 32.4 |
| 9 | 100 | 50.0 |
| 41 | 100 | 25.0 |
| 65 | 1 | 100 |
| 66 | 100 | 39.2 |
| 67 | 100 | 35.2 |
| 83 | 100 | 39.8 |
| 84 | 100 | 39.5 |
| 87 | 100 | 85.7 |
| 95 | 100 | 30.5 |
| 129 | 100 | 28.0 |
| 139 | 100 | 49.3 |
| 141 | 100 | 26.3 |
| 145 | 100 | 36.8 |
| 154 | 100 | 23.0 |
| 155 | 10 | 35.5 |
| 156 | 100 | 36.0 |

Test Example 2

(Cytotoxic Activity)

A culture medium containing a predetermined concentration of test compound was added to a 96-well plate (product of CORNING) in 100 μl/well. Then, Vero cells were adjusted to the concentration of $2\times10^4$ cells/mL with culture medium. The solution was added to the plate at 100 μL/well, and cultured at 37° C. in 5% $CO_2$-air atmosphere for 4 days. When the culture was completed, the number of alive cells was counted according to the XTT method [for example, see CANCER RESEARCH, Vol. 48, Pages 4827-4833 (1988)].

As a result, the 50% cell growth inhibitory concentration ($IC_{50}$) of 3-hydroxy-2-pyrazinecarboxamide (compound No. 1) was 250 μg/mL or more.

Test Example 3

(Anti-Rhino Activity)

The confluent monolayers of HeLa cells in 6-well tissue culture plates were inoculated with 70 PFU/well of rhino virus typeII strain. After 60 min, the inoculum was removed, and the test medium (E'MEM) containing the concentration of 30 μg/ml of compounds, 30 μg/ml DEAE-dextran, 30 mM $MgCl_2$, 3% basal medium Eagle vitamine solution, 2% fatal calf serum and 0.6% agarose were added. HeLa cells inoculated with rhino virus were incubated for 3 days at 33° C. under 100% humidity. After incubation period, the test plates were fixed with 3% formaldehyde solution and the overlay was removed. The cell-monolayer was stained with 0.05% methylene blue and the plaque numbers were counted. The inhibition percent were calculated from the number of plaque in the treated wells and that in the control wells.

The results are shown in Table 6, wherein the test compound number are the same as those in Tables 1 to 4.

TABLE 6

| No. | Inhibition percent (%) |
|---|---|
| 1 | 20.8 |
| 3 | 47.2 |
| 4 | 18.1 |
| 5 | 63.9 |
| 9 | 56.9 |
| 41 | 59.7 |
| 65 | 44.3 |
| 66 | 59.7 |
| 83 | 72.2 |
| 95 | 48.6 |
| 139 | 45.5 |
| 141 | 56.9 |

Test Example 4

(Anti-RSV Activity)

The confluent monolayers of Hep-2 cells in 6-well tissue culture plates were inoculated with 70 PFU/well of respiratory syncytial virus (RSV) A-2 strain. After 60 min, the inoculum was removed, and the test medium (E'MEM) containing the concentration of 30 μg/ml of compounds, 0.12% glutamine, 2% fatal calf serum and 1% methyl cellulose were added. Hep-2 cells inoculated with RSV were incubated for 3 days at 35° C. under 100% humidity. After incubation period, the test plates were fixed with 3% formaldehyde solution and the overlay was removed. The cell-monolayer was stained with Giemsa' solution and the plaque numbers were counted. The inhibition percent were calculated from the number of plaque in the treated wells and that in the control wells.

The results are shown in Table 7, wherein the test compound number are the same as those in Tables 1 to 4.

TABLE 7

| No. | Inhibition percent (%) |
|---|---|
| 1 | 61.4 |
| 6 | 72.8 |
| 65 | 74.3 |
| 67 | 72.4 |
| 86 | 74.1 |

Test Example 5

(Anti-BVDV Activity)

The confluent monolayers of MDBK cell in 6-well tissue culture plates were inoculated with 70 PFU/well of bovine viral diarrhea virus (BVDV) NADL strain. After 60 min, the inoculum was removed, and the test medium (E'MEM) containing the concentration of 30 μg/ml of compounds, 5% horse serum and 1% SeaPlaque Agar were added. MDBK cells inoculated with BVDV were incubated for 3 days at 35° C. under 100% humidity. After incubation period, the test plates were fixed with 3% formaldehyde solution, the overlay was removed, and the cells were stained with 1% crystal violet.

The inhibition percent were calculated from the number of plaque in the treated wells and that in the control wells.

The results are shown in Table 8, wherein the test compound number are the same as those in Tables 1 to 4.

TABLE 8

| No. | Inhibition percent (%) |
|---|---|
| 1 | 0 |
| 65 | 35.1 |

BEST MODE FOR CARRYING OUT THE INVENTION

Next, the compound of the present invention is explained with reference to Referential Examples and Examples. The invention is by no means limited by these examples.

In the eluent, the mixing ratios are all by volume.

The carrier used in column chromatography was Silica Gel BW-127ZH (product of Fuji Silicia Chemical Co.), and the carrier used in the reverse phase column chromatography was LC-SORB SP-B-ODS (product of Chemco Co.).

The symbol mark used in the Referential Examples and Examples has the following meaning:

DMSO-$d_6$: Deuterated dimethyl sulfoxide

Referential Example 1

In 6 mL of dichloromethane is suspended 0.30 g of methyl 3-hydroxy-2-pyrazinecaroxylate obtained according to the method described in literature [J. Heterocycl. Chem., 34, 27 (1997)]. To the suspension are successively added 0.54 ml. of triethylamine and 0.29 g of glycine methyl ester hydrochloride. The resulting mixture is stirred at ambient temperature for 5 hours. After cooling, the solvent is distilled off under reduced pressure. The residue is purified by reverse phase column chromatography (eluent: water) to obtain 0.16 g of methyl 2-{[(3-hydroxy-2-pyrazinyl)-carbonyl] amino}acetate.

IR(KBr) $cm^{-1}$: 1750, 1735, 1685

NMR(DMSO-$d_6$) δ value: 3.67(3H, s), 4.12(2H,d,J=6 Hz), 7.70-8.30(2H,m), 9.60-10.10(1H,m), 13.10(1H,brs)

Referential Example 2

In 100 ml of concentrated sulfuric acid is dissolved 17.00 g of methyl 6-bromo-3-amino-2-pyrazinecarboxylate obtained according to the method described in literature [J. Am. Chem. Soc., 2798-2800 (1949)]. At an ice-cooled temperature, 10.11 g of sodium nitrite is added to the suspension, which is stirred for 30 minutes. The reaction mixture is poured into 920 mL of methanol, and heated under reflux for 5 hours. The reaction mixture is cooled and then concentrated under reduced pressure. The residue thus obtained is added to a mixture of 500 mL of ice water and 600 mL of chloroform and separated into layers. The organic layer is washed successively with saturated aqueous solution of sodium hydrogen carbonate, water and saturated aqueous solution of sodium chloride and dried over anhydrous magnesium sulfate. Then, the solvent is distilled off under reduced pressure to obtain 6.30 g of methyl 6-bromo-3-methoxy-2-pyrazinecarboxylate.

IR(KBr) $cm^{-1}$: 1734

NMR($CDCl_3$) δ value: 3.97(3H,s), 4.06(3H,s), 8.37(1H,s)

Referential Example 3

In a nitrogen atmosphere, 11.38 g of methyl 6-bromo-3-methoxy-2-pyrazinecarboxylate is dissolved in 227 mL of toluene. To the solution are successively added 10.32 g of benzophenone-imine, 0.42 g of tris(dibenzylideneacetone) dipalladium, 0.86 g of (s)-(−)-2,2'-bis(diphenylphosphino)-1,1'-binaphthyl and 6.20 g of sodium t-butoxide. The resulting mixture is stirred at 80° C. for one hour. The reaction mixture is cooled and filtered. The filtrate is purified by column chromatography (eluent: toluene:ethyl acetate=20:1). The oily product thus obtained is dissolved in 140 mL of tetrahydrofuran, 7 mL of 2 mol/mL hydrochloric acid is added thereto and the resulting solution is stirred at ambient temperature for 15 minutes. A mixture of 200 mL of chloroform and 50 mL of water is added to the resulting reaction mixture, and alkalified with 1 mol/mL of sodium hydroxide, and the organic layer is separated. The organic layer is washed with saturated aqueous solution of sodium chloride, dried over anhydrous magnesium sulfate, and the solvent is distilled off under reduced pressure. The residue thus obtained is purified by column chromatography (eluent: toluene:ethyl acetate 1:1) to obtain 3.64 g of methyl 6-amino-3-methoxy-2-pyrazinecarboxylate.

IR(KBr) $cm^{-1}$: 1716,1670

NMR(DMSO-$d_6$) δ value: 3.80(3H,s), 3.82(3H,s), 7.20 (2H,brs), 7.77(1H,s)

Referential Example 4

In 70 mL of methanol is dissolved 3.50 g of methyl 6-amino-3-methoxy-2-pyrazinecarboxylate. Gaseous ammonia is introduced to saturate the solution with ammonia. The solution is stirred at ambient temperature for 14 hours. The solvent is distilled off from the reaction mixture under reduced pressure to obtain 3.1 g of 6-amino-3-methoxy-2-pyrazinecarboxamide.

IR(KBr) $cm^{-1}$: 1684

NMR(DMSO-$d_6$): 3.79(3H,s), 5.87(2H,brs), 7.30-7.75 (3H,m)

Referential Example 5

In a nitrogen atmosphere, 1.50 g of 6-amino-3-methoxy-2-pyrazinecarboxamide is dissolved in 12 mL of 70% pyridine hydrofluoride under ice-cooling. Then, 0.71 g of sodium nitrite is added thereto at −50° C., and the resulting solution is stirred at 10° C. for 1 hour. The resulting reaction mixture is stirred at ambient temperature for an additional 1 hour. Thereafter, a mixture of 50 mL of ice water and 100 mL of chloroform is added thereto and the resulting mixture is separated into layers. The organic layer is washed with saturated aqueous solution of sodium chloride and saturated aqueous solution of sodium hydrogen carbonate, and dried over anhydrous magnesium sulfate. Then, the solvent is distilled off under reduced pressure to obtain 1.29 g of 6-fluoro-3-methoxy-2-pyrazinecarboxamide.

IR(KBr) $cm^{-1}$: 1706

NMR(DMSO-$d_6$): 3.95(3H,s), 7.55-8.15(2H,m), 8.39 (1H,d,J=8.3 Hz)

Referential Example 6

In 100 mL of methanol is suspended 1.96 g of methyl 5-amino-3-methoxy-2-pyrazinecarboxylate obtained according to the method described in literature (JP-A-50-105675). The resulting suspension is saturated with ammonia by introducing gaseous ammonia thereinto at −20° C. Then, the solution thus obtained is allowed to react at 95° C. for 24 hours in a stainless steel-made closed vessel. After cooling, the solvent is distilled off under reduced pressure to obtain 1.57 g of 5-amino-3-methoxy-2-pyrazinecarboxamide.

IR(KBr) $cm^{-1}$: 1654, 1637

NMR(DMSO-$d_6$) δ value: 3.82(3H,s), 7.00(3H,brs), 7.30 (1H,brs), 7.43(1H,s)

Referential Example 7

In a nitrogen atmosphere, 0.5 g of 5-amino-3-methoxy-2-pyrazinecarboxamide is dissolved in 9 mL of 70% pyridine hydrofluoride under ice-cooling. Then, 0.23 g of sodium nitrite is added thereto at −70° C., and the resulting solution is heated to a temperature of −10° C. in 30 minutes. Further, the solution is stirred at ambient temperature for 30 minutes. A mixture of 30 mL of ice water and 100 mL of chloroform is added thereto and the resulting mixture is separated into layers. The organic layer is washed with saturated aqueous solution of sodium chloride and dried over anhydrous magnesium sulfate. The solvent is distilled off under reduced pressure. The residue thus obtained is purified by column chromatography (eluent: chloroform:methanol =10:1) to obtain 0.37 q of 5-fluoro-3-methoxy-2-pyrazinecarboxamide.

IR(KBr) $cm^{-1}$: 1705

NMR(DMSO-$d_6$) δ value: 3.94(3H,s), 7.65(1H,brs), 7.85 (1H,brs), 8.12(1H,d,J=8.3 Hz)

EXAMPLE 1

In 3 mL of methanol is suspended 0.6 g of methyl 6-bromo-3-hydroxy-2-pyrazinecarboxylate obtained according to the method described in literature [J. Med. Chem., 1969, 12(2), 285-287]. Then, 6 mL of 25% aqueous ammonia is added thereto and the resulting solution is stirred at ambient temperature for 17 hours. The reaction mixture is adjusted to pH 3 by adding 6 mol/L hydrochloric acid. The solvent is distilled off under reduced pressure. Isopropyl ether and water are added to the residue and filtered to obtain 0.33 g of 6-bromo-3-hydroxy-2-pyrazinecarboxamide.

IR(KBr) $cm^{-1}$: 1700, 1665

NMR(DMSO-$d_6$) δ value: 7.50(2H,brs), 8.08(1H,s), 9.95 (1H,brs)

EXAMPLE 2

In 10 mL of dimethylformamide is suspended (0.5 g of 3,5-dihydroxy-1,2,4-triazine-6-carboxylic acid obtained according to the method described in literature (JP-A-54-79292). Then, 2.06 g of N,N'-carbonyldiimidazole is added thereto, and the resulting solution in stirred at ambient temperature for 6 hours. The reaction mixture is cooled with ice, saturated with gaseous ammonia, and then stirred for 15 minutes at the same temperature as above. The deposited crystals are collected by filtration to obtain 0.37 g of 3,5-dioxo-2,3,4,5-tetrahydro-1,2,4-triazine-6-carboxamide.

IR(KBr) $cm^{-1}$: 1732, 1710, 1685, 1656

NMR(DMSO-$d_6$) δ value: 7.75(1H,s), 7.97(1H,s), 12.20-12.80(2H,m)

EXAMPLE 3

In 5 mL of acetic anhydride is suspended 0.5 g of 3-hydroxy-2-pyrazinecarboxamide. The resulting solution is stirred at 110° C. for 1 hour. The deposited crystals are collected by filtration to obtain 0.5 g of $N^2$-acetyl-3-hydroxy-2-pyrazinecarboxamide.

IR(KBr) $cm^{-1}$: 1725, 1695, 1655

NMR(DMSO-$d_6$) δ value: 2.25(3H,s), 7.53(1H,d,J=4 Hz), 7.69(1H,d,J=4 Hz), 11.70(1H,brs)

EXAMPLE 4

In 5 mL of 25% aqueous ammonia is suspended 0.25 g of methyl 6-chloro-3-hydroxy-2-pyrazinecarboxylate obtained according to the method described in literature [J. Med. Chem., 285-287 (1969)]. The suspension is stirred at ambient temperature for 1 hour. The deposited crystals are collected by filtration to obtain 0.18 g of 6-chloro-3-hydroxy-2-pyrazinecarboxamide.

IR(KBr) $cm^{-1}$: 1652

NMR(DMSO-$d_6$): 7.22(2H,brs), 7.91(1H,s), 10.40(1H, brs)

EXAMPLE 5

In 50 mL of tetrahydrofuran is suspended 1.00 g of 3-hydroxy-2-pyrazinecarboxamide. Then, 3.5 mL of triethylamine and 1.67 mL of benzoyl chloride are successively added thereto. The resulting solution is stirred at 60° C. for 5 hours and cooled. The deposited crystals are collected by filtration. The crystals thus obtained are suspended in a mixture of 8 mL of water and 1 mL of 1 mol/mL hydrochloric acid, stirred at ambient temperature for 30 minutes, and collected by filtration to obtain 0.41 g of $N^2$-benzoyl-3-hydroxy-2-pyrazinecarboxamide.

IR(KBr) $cm^{-1}$: 1735

NMR(DMSO-$d_6$) δ value: 7.20-8.40(7H,m), 12.60(1H, brs)

According to the same method as above, $N^2$-(2,2-dimethylpropanoyl)-3-hydroxy-2-pyrazinecarboxamide is obtained.

IR(KBr) $cm^{-1}$: 1725

NMR(DMSO-$d_6$) δ value: 1.21(9H,s), 7.49(1H,d, J=2 Hz), 7.95(1H,d,J=2 Hz), 14.80(1H,brs)

EXAMPLE 6

In 0.5 mL of 47% aqueous solution of hydrogen bromide is dissolved 0.05 g of 3-methoxy-2-pyrazinecarboxamide-4-oxide obtained according to the method described in literature [Eur. J. Med. Chem., 15(2), 157-163 (1980)]. The solution is stirred at 45° C. for 2 hours. The deposited crystals are collected by filtration and washed successively with ethanol and diethyl ether to obtain 0.03 g of 3-hydroxy-2-pyrazinecarboxamide-4-oxide.

IR(KBr) $cm^{-1}$: 1695

NMR(DMSO-$d_6$) δ value: 7.19(1H,d,J=6 Hz), 7.56(1H, d,J=6 Hz), 7.70(1H,brs), 7.95(1H,brs), 10.75(1H,brs)

EXAMPLE 7

In 4 mL of methanol is suspended 0.19 g of methyl 2-{[(3-hydroxy-2-pyrazinyl)carbonyl]-amino}acetate. The suspension is saturated with ammonia by introducing gaseous ammonia thereinto under ice-cooling for 30 minutes. The resulting mixture is stirred at the same temperature as above for 1 hour and then at ambient temperature for 15 hours. The solvent is distilled off under reduced pressure. The residue thus obtained is dissolved in a mixture of 4 mL of water and 1 mL of methanol. To the resulting solution is added 0.9 mL of 1 mol/L hydrochloric acid. The deposited crystals are collected by filtration to obtain 0.16 g of $N^2$-(2-amino-2-oxoethyl)-3-hydroxy-2-pyrazinecarboxamide.

IR(KBr) $cm^{-1}$: 1675

NMR(DMSO-$d_6$) δ value: 3.90(1H,d,J=5 Hz), 7.10(1H, brs), 7.40(1H,brs), 7.60-8.40(2H,m), 9.50(1H,brs), 13.0 (1H, brs)

EXAMPLE 8

In a nitrogen atmosphere, 1.51 g of sodium iodide is dissolved in 22 mL of acetonitrile. Then, 1.10 g of trimethylsilyl chloride is added thereto. The resulting solution is stirred at ambient temperature for 20 minutes. Then, 0.43 g of 6-fluoro-3-methoxy-2-pyrazinecarboxamide is added thereto. The resulting solution is stirred at the same temperature as above for 18 hours. Then, a mixture of 10 mL of water and 200 mL of chloroform is added to the reaction mixture, and separated into layers. The organic layer thus obtained is washed successively with 5% aqueous solution of sodium thiosulfate and saturated aqueous solution of sodium chloride, and dried over anhydrous magnesium sulfate. The solvent is distilled off under reduced pressure. The residue thus obtained is purified by column chromatography (eluent: hexane:ethyl acetate=2:1) to obtain 0.06 g of 6-fluoro-3-hydroxy-2-pyrazinecarboxamide.

IR(KBr) $cm^{-1}$: 1685, 1670, 1656

NMR($CDCl_3$): 5.40-7.80(2H,m), 8.31(1H,d,J=7.82 Hz), 12.33(1H,s)

EXAMPLE 9

In 24 mL of concentrated sulfuric acid is suspended 4.00 g of 3-hydroxy-2-pyrazinecarboxamide. To the suspension is added 3.09 g of potassium nitrate under ice-cooling. The resulting mixture is stirred at 40° C. for 3 hours. The reaction mixture is poured into 240 mL of water, and the deposited crystals are collected by filtration. The crystals thus obtained are suspended in 80 mL of water and heated under reflux for 30 minutes. After cooling, the crystals are collected by filtration to obtain 2.45 g of 3-hydroxy-6-nitro-2-pyrazinecarboxamide.

IR(KBr) $cm^{-1}$: 1705, 1685, 1655

NMR(DMSO-d6) δ value: 8.10(1H,brs), 8.30(1H,brs), 8.96(1H,s)

EXAMPLE 10

In 2.1 mL of water is suspended 0.5 g of 2-aminomalonamide. Under ice-cooling, 0.43 g of ethyl glyoxalate is added to the suspension, which is then stirred for 40 minutes. Then, 0.85 mL of 5 mol/mL sodium hydroxide is added to the resulting suspension, which is then stirred at the same temperature as above for 40 minutes. The reaction mixture is adjusted to pH 12 by adding 1 mol/L sodium hydroxide, and once made into a solution. The solution is then adjusted to pH 2 by adding 6 mol/mL hydrochloric acid. The deposited crystals are collected by filtration and washed successively with water and 50% (w/w) ethanol to obtain 0.15 g of 3,5-dihydroxy-2-pyrazinecarboxamide.

IR(KBr) $cm^{-1}$: 1660

NMR($D_2O$) δ value: 6.97(1H,s)

EXAMPLE 11

In 2.0 mL of water are suspended 0.65 mL of diethyl-2-oxomalonate and 0.5 g of 2-aminomalonamide. Under ice-cooling, 0.85 mL of 5 mol/mL sodium hydroxide is added thereto. The resulting solution is stirred for 40 minutes. Then, at ambient temperature, 2.55 mL of 5 mol/mL sodium hydroxide is added to the solution, which is then stirred for an additional 30 minutes. Ethanol is added to the reaction mixture and the precipitate is collected by filtration to obtain 0.24 g of 3,5-dihydroxy-6-ethoxycarbonyl-2-pyrazinecarboxamide.

IR(KBr) $cm^{-1}$: 1655, 1735

NMR($D_2O$) δ value: 1.17(3H,t,J=7 Hz), 4.15(2H,q,J=7 Hz)

EXAMPLE 12

In a mixture of 1.0 mL of water and 1.0 mL of ethanol is suspended 0.13 g of 3,5-dihydroxy-6-ethoxycarbonyl-2-pyrazinecarboxamide. At ambient temperature, 0.34 mL of 5 mol/mL sodium hydroxide is added to the suspension, which is then stirred for 16 hours. The reaction mixture is adjusted to pH 2 by adding 1 mol/mL hydrochloric acid. The deposited crystals are collected by filtration and washed with water to obtain 0.07 g of 3,5-dihydroxy-6-carboxy-2-pyrazinecarboxamide.

IR(KBr) $cm^{-1}$: 1650

EXAMPLE 13

In a nitrogen atmosphere, 0.09 g of 5-fluoro-3-methoxy-2-pyrazinecarboxamide is suspended in 3.6 mL of acetonitrile. Then, 0.16 g of sodium iodide and 0.11 g of chlorotrimethylsilane are successively added to the suspension, which is then stirred at ambient temperature for 20 hours. Then, 2 mL of water and 40 mL of chloroform are added to the reaction mixture and separated into layers. The organic layer is separated, washed successively with 5% (w/v) aqueous solution of magnesium thiosulfate and saturated aqueous solution of sodium chloride and dried over anhydrous magnesium sulfate. Then, the solvent is distilled off under reduced pressure. The residue thus obtained is purified by column chromatography (eluent: chloroform) to obtain 0.01 g of 5-fluoro-3-hydroxy-2-pyrazinecarboxamide.

IR(KBr) $cm^{-1}$: 1670

NMR($CDCl_3$) δ value: 5.80(1H,s), 7.45(1H,brs), 7.93 (1H, d,J=7.8 Hz), 12.93(1H,s)

EXAMPLE 14

In 5 mL of ethanol is dissolved 0.1 g of ethyl 5-oxo-3-thioxo-2,3,4,5-tetrahydro-1,2,4-triazine-6-carboxylate obtained according to the method described in literature (J. Am. Chem. Soc., 1956, 78, 1258-1259). At ambient temperature, gaseous ammonia is introduced into the solution for 30 minutes to saturate the solution with ammonia. After allowing the solution to stand at the same temperature as above for 15 hours, the resulting crystals are collected by filtration. The crystals thus collected are washed with three 5 mL portions of ethanol to obtain 0.05 g of 5-oxo-3-thioxo-2,3,4,5-tetrahydro-1,2,4-triazine-6-carboxamide.

IR(KBr) $cm^{-1}$: 1654

NMR(DMSO-$d_6$) δ value: 3.30(4H,brs)

EXAMPLE 15

According to the method described in literature (International Patent Application: WO 98130549), 6-oxo-1,6-dihydro-5-pyrimidinecarboxamide is obtained.

EXAMPLE 16

According to the method described in literature (Chemische Berichte, 1964, 97, 3349-3353), 3-oxo-2,3-dihydro-4-pyridazinecarboxamide is obtained.

EXAMPLE 17

In 5 mL of ethanol is dissolved 0.06 g of ethyl 5-oxo-4,5-dihydro-1,2,4-triazine-6-carboxylate. At 10° C., the solution is saturated with ammonia by introducing gaseous ammonia thereinto for 20 minutes. The solution is allowed to stand at ambient temperature for 15 hours, and the resulting crystals are collected by filtration. The crystals thus obtained are washed successively with two 2 mL portions of ethanol and then two 1 mL portion of methanol to obtain 0.03 g of 5-oxo-4,5-dihydro-1,2,4-triazine-6-carboxamide.

IR(KBr) $cm^{-1}$: 1654

NMR(DMSO-$d_6$) δ value: 3.60(1H,brs), 7.44(1H,brs), 8.39(1H,s), 9.74(1H,brs)

EXAMPLE 18

In 4 mL of dimethyl sulfoxide is dissolved 0.4 g of methyl 3-hydroxy-2-pyrazinecarboxlate. Then, 0.27 g of L-aspartic acid and 0.85 mL of triethylamine are successively added to the solution, which is then stirred at 50° C. for 6 hours. The deposited crystals are filtered off, and the filtrate is concentrated under reduced pressure. Then, 2 mL of water and 0.2 mL of methanol are added to the resulting residue. The precipitate formed is collected by filtration to obtain 0.09 g of (2S)-2-{[(3-oxo-3,4-dihydro-2-pyrazinyl)-carbonyl] amino}-butanedioic acid.

IR(KBr) $cm^{-1}$: 1695, 1680, 1665

NMR(DMSO-$d_6$) δ value: 2.83(2H,d,J=5 Hz), 4.50-5.00 (1H,m), 7.60-8.05(2H,m), 9.95(1H,d,J=9 Hz), 12.90(3H, brs)

EXAMPLE 19

In 5 mL of dimethyl sulfoxide is dissolved 0.42 g of L-alanyl-L-alanine trifluoroacetate. Then, 1.07 mL of triethylamine and 0.71 g of methyl 3-hydroxy-2-pyrazinecarboxylate are successively added to the solution, which is then stirred at 40° C. for 17 hours. The solvent is distilled off under reduced pressure, and 2 mL of water was added to the residue thus obtained. The deposited product is collected by filtration and purified by column chromatography [eluent: chloroform: methanol=30:1) to obtain 0.035 g of (2S)-2-[((2S)-2-{[(3-oxo-3,4-dihydro-2-pyrazinyl) carbonyl]amino}-propanoyl) amino]propanoic acid.

IR(KBr) $cm^{-1}$: 1665, 1675, 1655

NMR(DMSO-$d_6$) δ value: 1.28(3H,d,J=7 Hz), 1.32(3H, d,J=7 Hz), 3.95-4.95(2H,m), 5.1(2H,brs), 7.71(1H,d,J=3 Hz), 7.87(1H,d,J=3 Hz), 8.32(1H,d,J=7 Hz), 9.9(1H,brs)

INDUSTRIAL APPLICABILITY

An antiviral agent comprising the nitrogen-containing heterocyclic carboxamide derivative represented by general formula [1] or a salt thereof is useful for preventing and treating virus-infections and especially influenza virus-infections.

What is claimed is:

1. A nitrogen-containing heterocyclic carboxamide compound represented by the following formula

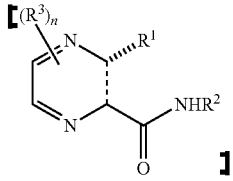

]

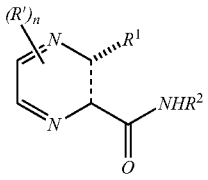

wherein:

each occurrence of [$R^3$] *R′* is [independently] a halogen atom[,] *or* a hydroxyl group, [or an oxide group] *which is linked to a carbon atom of the nitrogen-containing heterocycle in said formula*;

$R^1$ represents O or OH;

$R^2$ is selected from the group consisting of a hydrogen atom, an acyl group, an optionally substituted carbamoylalkyl group, and an optionally substituted carboxyalkyl group;

n is 1[,] *or* 2[, 3, or 4]; [and]

the broken line in the ring represents a single bond when $R^1$ is O and a double bond when $R^1$ is OH; *and*

*the broken line between $R^1$ and the ring is a single bond when $R^1$ is OH and a double bond when $R^1$ is O;* or a pharmaceutically acceptable salt thereof.

2. The nitrogen-containing heterocyclic carboxamide compound according to claim 1 wherein:

[at least one occurrence of $R^3$] *R′* is a halogen atom, *which is linked to a carbon atom of the nitrogen-containing heterocycle in said formula*; and $R^2$ is a hydrogen atom.

3. A method of treating a viral [condition] *infection* associated with influenza virus, C-type hepatitis, rhino virus, or respiratory syncytial virus by administering, to a patient in need thereof, an effective amount of [at least one compound or a pharmaceutically acceptable salt thereof, the compound having a structure according to] *a compound represented by* the following formula

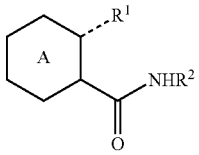

wherein:

ring A represents [a pyrazine, pyrimidine, pyridazine or triazine ring,] *a ring selected from the group consisting of*

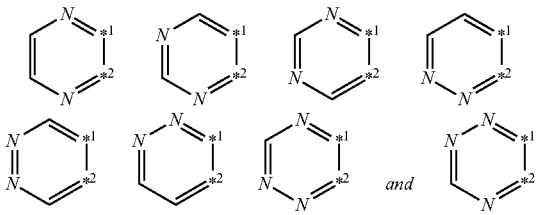

*wherein:*

*the mark *1 expresses the position of substitution with $R^1$;*

*the mark *2 expresses the position of substitution with —C(=O)NHR²;* ring A is optionally substituted with [at least] one of a halogen atom, a hydroxyl group, [an oxide group,] a phenyl group, a pyridinyl group, and a mercapto group, *which is linked to a carbon atom of ring A*;

$R^1$ represents [O or] OH;

$R^2$ is selected from the group consisting of a hydrogen atom, an acyl group, an optionally substituted carbamoylalkyl group, and an optionally substituted carboxyalkyl group; and the broken line is [one of] a single bond [and a double bond]; *or a pharmaceutically acceptable salt thereof.*

[4. The method according to claim 3, wherein:

said ring A represents a pyrazine, pyrimidine, or triazine ring, ring A is optionally substituted with at least one of a halogen atom, a hydroxyl group, an oxide group, a phenyl group, a pyridinyl group, and a mercapto group.]

5. The method according to [claim 4] *claim 3*, wherein[:] said ring A represents *the following ring*

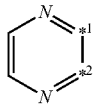

[a pyrazine ring,] ring A is optionally substituted with [at least] one of a halogen atom, a hydroxyl group, [an oxide group,] a phenyl group, a pyridinyl group, and a mercapto group, *which is linked to a carbon atom of ring A.*

6. The method according to claim 3, wherein said viral [condition] *infection* is associated with influenza virus.

7. A pharmaceutical composition comprising:

a therapeutically effective amount of a compound according to claim 1, and a pharmaceutically acceptable carrier or diluent.

8. The method according to claim 3, wherein said viral [condition] *infection* is associated with C-type hepatitis.

9. The method according to claim 3, wherein said viral [condition] *infection* is associated with rhino virus.

10. The method according to claim 3, wherein said viral [condition] *infection* is associated with respiratory syncytial virus.

11. The method according to claim 3, wherein the compound has the formula

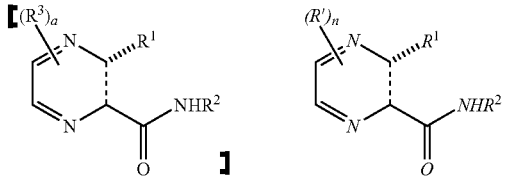

wherein:

each occurrence of [$R^3$] $R'$ is [independently] a halogen atom[,] *or* a hydroxyl group, [or an oxide group] *which is linked to a carbon atom of the nitrogen-containing heterocycle in said formula*;

$R^1$ represents O or OH;

$R^2$ is selected from the group consisting of a hydrogen atom, an acyl group, an optionally substituted carbamoylalkyl group, and an optionally substituted carboxyalkyl group;

n is 1 or 2; [and]

the broken line in the ring represents a single bond when $R^1$ is O and a double bond when $R^1$ is OH; *and*

*the broken line between $R^1$ and the ring is a single bond when $R^1$ is OH and a double bond when $R^1$ is O;* or a pharmaceutically acceptable salt thereof.

12. The method according to claim 11, wherein said viral [condition] *infection* is associated with influenza virus.

13. The method according to claim 11, wherein said viral [condition] *infection* is associated with C-type hepatitis.

14. The method according to claim 11, wherein said viral [condition] *infection* is associated with rhino virus.

15. The method according to claim 11, wherein said viral [condition] *infection* is associated with respiratory syncytial virus.

16. The method according to claim 3, wherein *said* ring A represents [a pyrazine, pyrimidine, pyridazine or triazine ring,] *a ring selected from the group consisting of*

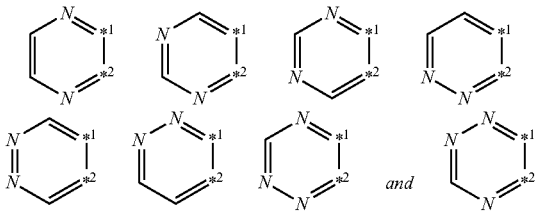

ring A is [optionally] substituted with [at least] one of a halogen atom, a hydroxyl group, a phenyl group, a pyridinyl group, and a mercapto group, *which is linked to a carbon atom of ring A.*

[17. The method according to claim 4, wherein ring A represents a pyrazine, pyrimidine, or triazine ring, ring A is optionally substituted with at least one of a halogen atom, a hydroxyl group, a phenyl group, a pyridinyl group, and a mercapto group.]

18. The method according to claim [5] *3*, wherein *said* ring A represents [a pyrazine ring] *the following ring,*

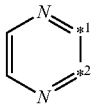

ring A is optionally substituted with [at least] one of a halogen atom[,] *or* a hydroxyl group, [and an oxide group] *which is linked to a carbon atom of ring A.*

*19. The compound of claim 1 wherein:*

*R′ is fluorine, which is linked to a carbon atom of the nitrogen-containing heterocycle in said formula,*

*$R^2$ is hydrogen, and*

*n is 1.*

*20. A nitrogen-containing heterocyclic carboxamide compound represented by the following formula*

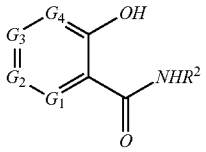

*wherein $G_1$ and $G_4$ are N, $G_2$ is C—F, $G_3$ is CH, and $R^2$ is hydrogen,*

*or a pharmaceutically acceptable salt thereof.*

*21. A method of treating a viral infection associated with influenza virus, C-type hepatitis, rhino virus, or respiratory syncytial virus by administering, to a patient in need thereof, an effective amount of a compound represented by the following formula*

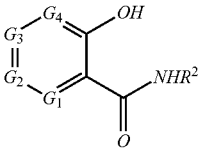

*wherein $G_1$ and $G_4$ are N, $G_2$ is C—F and $G_3$ is CH, and $R^2$ is hydrogen,*

*or a pharmaceutically acceptable salt thereof.*

*22. The method according to claim 21, wherein said viral infection is associated with influenza virus.*

*23. The method according to claim 21, wherein said viral infection is associated with C-type hepatitis.*

*24. The method according to claim 21, wherein said viral infection is associated with rhino virus.*

*25. The method according to claim 21, wherein said viral infection is associated with respiratory syncytial virus.*

*26. A pharmaceutical composition comprising: a therapeutically effective amount of a compound according to claim 20, and a pharmaceutically acceptable carrier or diluent.*

* * * * *